US006186968B1

(12) United States Patent
Wu

(10) Patent No.: US 6,186,968 B1
(45) Date of Patent: Feb. 13, 2001

(54) FOLDABLE ELECTRIC TRACTION MACHINE

(75) Inventor: Jack Wu, Taipei (TW)

(73) Assignee: Modas Shing Company Ltd., Taipei (TW)

( * ) Notice: Under 35 U.S.C. 154(b), the term of this patent shall be extended for 0 days.

(21) Appl. No.: 09/223,866

(22) Filed: Dec. 31, 1998

(51) Int. Cl.$^7$ .......... A61F 5/00

(52) U.S. Cl. .......... 602/32; 602/35; 606/241; 606/245

(58) Field of Search .......... 602/32, 33, 35, 602/36, 38; 601/23, 24, 26; 606/241, 242, 243, 244, 245; 5/620, 612, 613, 617, 618; 482/97, 142, 130, 133, 134

(56) References Cited

U.S. PATENT DOCUMENTS

| | | | | |
|---|---|---|---|---|
| 1,331,041 | * | 2/1920 | Anderson | 5/612 |
| 4,435,861 | * | 3/1984 | Lindley | 5/612 |
| 4,943,041 | * | 7/1990 | Romein | 5/620 |
| 4,951,654 | * | 8/1990 | Gambale et al. | 606/242 |
| 5,320,640 | * | 6/1994 | Riddle et al. | 606/242 |
| 5,335,676 | * | 8/1994 | O'Brien | 5/620 |
| 5,466,205 | * | 11/1995 | McLane et al. | 482/140 |
| 5,478,307 | * | 12/1995 | Wang | 602/32 |
| 5,674,167 | * | 10/1997 | Piaget et al. | 482/130 |

* cited by examiner

*Primary Examiner*—Mickey Yu
*Assistant Examiner*—Justine R. Yu
(74) *Attorney, Agent, or Firm*—Trask Britt

(57) ABSTRACT

An foldable electric traction machine comprises a front beam, a rear beam and a joint connecting the front beam and the rear beam. A motor is mounted beneath the rear beam. A sliding bracket is mounted on an extension beam and can be moved by the motor. The body of a patient lying on the traction machine will be stretched by the motor driving the sliding bracket along the extension beam. A rope is provide under the front and the rear beam and will be gradually tensioned with the movement of the sliding bracket. Therefore, when the motor is operated, the traction machine not only can improve the user's body condition, but also raise the user's waist.

12 Claims, 6 Drawing Sheets

FOLDABLE ELECTRIC TRACTION MACHINE

BACKGROUND OF THE INVENTION

1. Field of the Invention

The present invention relates to a foldable electrical traction machine, and more particularly to a traction machine which can ease the pain of a patient with bone spurs or protrusion of the intervertebral disc.

2. Description of Related Art

Bone spurs are a common condition in old people. In addition, office workers and computer users have a great risk of having protrusion of the intervertebral disc. Based on a patient's condition, a doctor can use different treatments for the patient's condition. In general, the doctor will use physiotherapy and not operate on a patient unless his condition is very serious. Therefore, there are many therapeutic apparatus to assist a patient to ease pain and gradually recover health.

Because a patient's vertebra is pressed for a long period of time, stretching the patient's body, especially the spine, can really relax nerves of the vertebra. A conventional traction machine can accomplish the purpose. The conventional traction machine provides a pad and a movable foot holder mounted on an end of the pad. The patient can lie down on the pad and move the foot holder away by a handle. Therefore, the patient's vertebra can be stretched.

However, the traction machine can not be folded as it is a fixed structure. This machine only provides a stretching function and its use is limited. Furthermore, if the patient does not have enough strength in his/her arms, the machine can not be used.

A foldable electrical traction machine in accordance with the present invention tends to mitigate and/or obviate the aforementioned problem.

SUMMARY OF THE INVENTION

The main object of the present invention is to provide a traction machine which can be folded for storing.

Another object of the present invention is to provide a traction machine which can be operated by a motor.

A further object of the present invention is to provide a traction machine which can lift a patient's waist.

Other objects, advantages and novel features of the invention will become more apparent from the following detailed description when taken in conjunction with the accompanying drawings.

DETAILED DESCRIPTION OF THE PREFERRED EMBODIMENT

Figure 1:
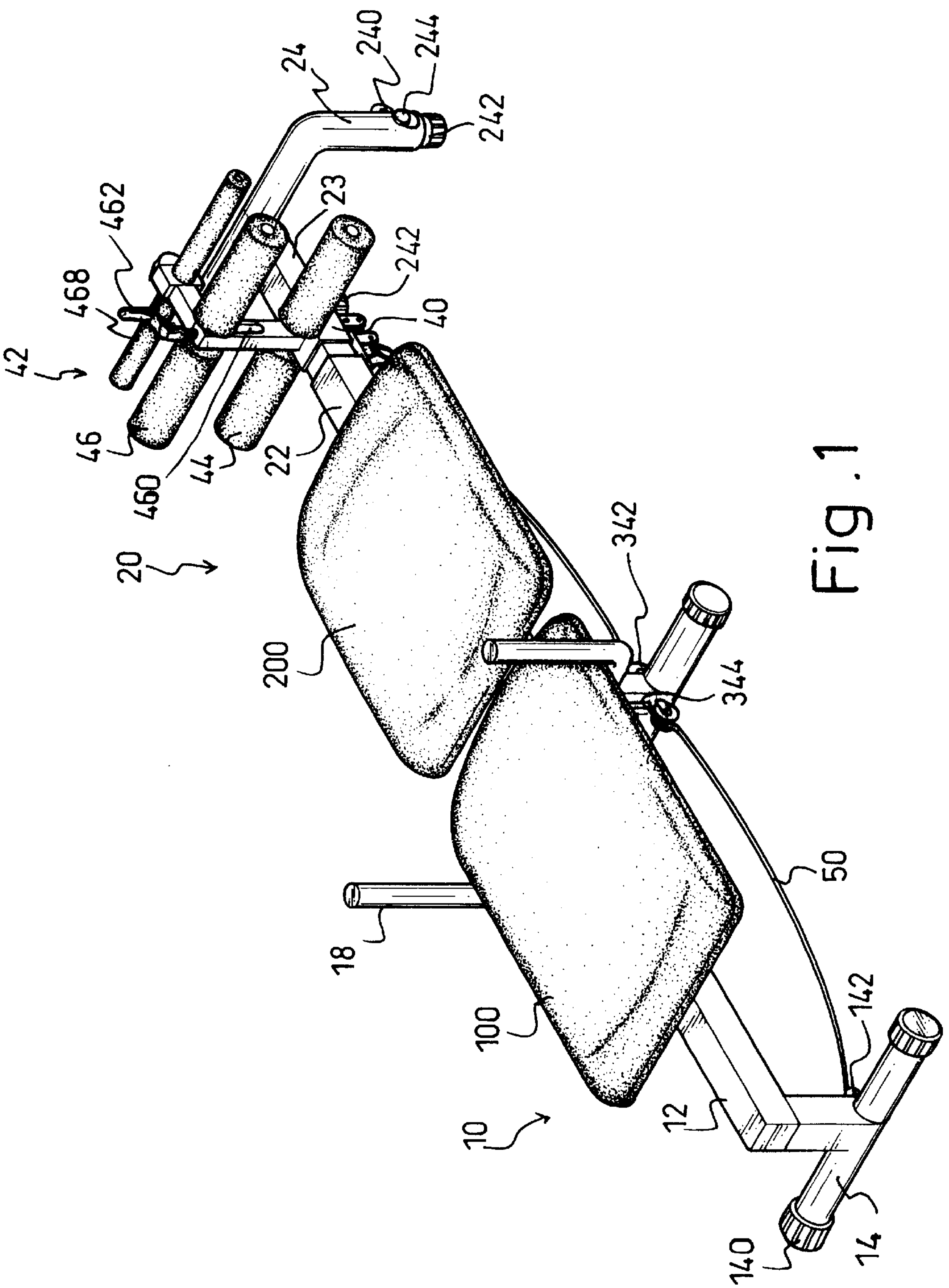
FIG. 1 is a perspective view of the present invention.

A preferred embodiment of the present invention is shown in FIG. 1. The whole profile of the traction machine is similar to that of a conventional one.

The traction machine of the present invention is constructed by a front frame (10), a rear frame (20) and a joint (30) engaging the front and rear frame (10, 20), as shown in FIG. 1.

Figure 2:
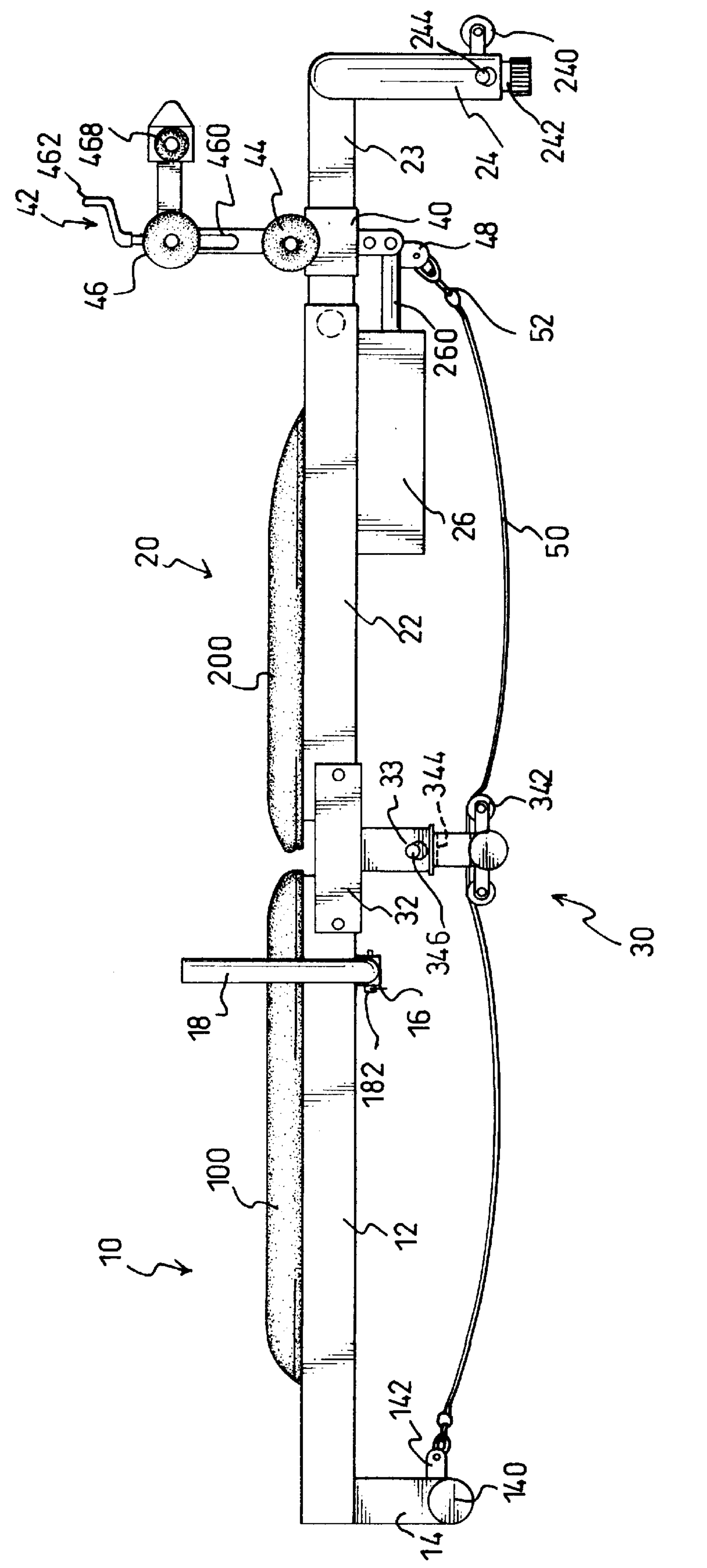
FIG. 2 is a side view of the present invention.
Figure 6:
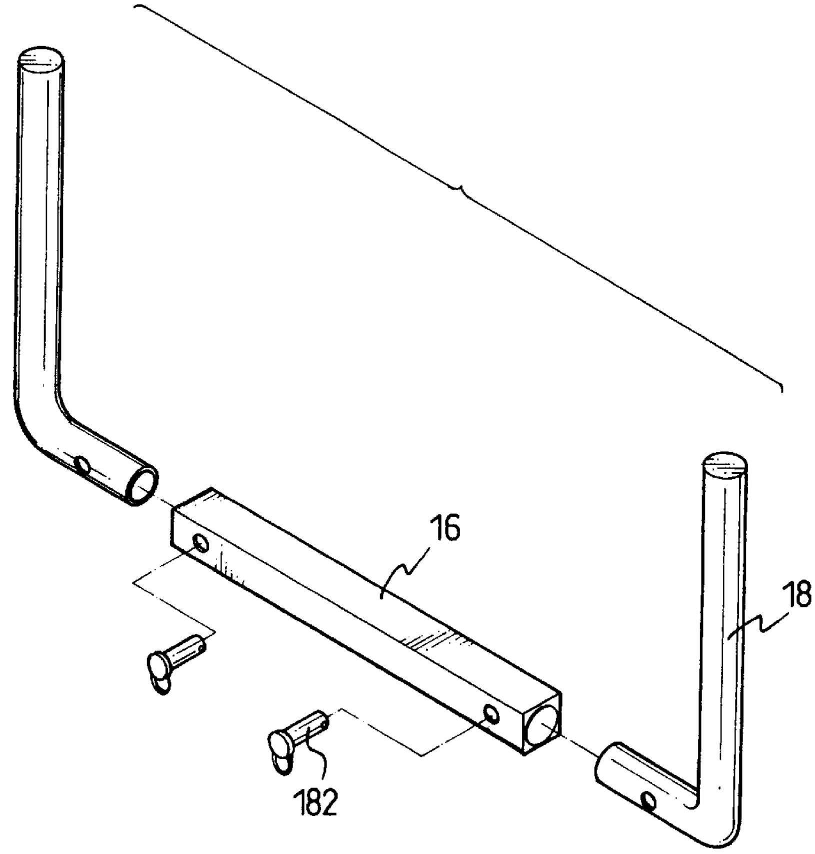
FIG. 6 is a exploded view showing a handle of the present invention.

Referring to FIG. 2, the front frame (10) has a front beam (12) securely attached therewith. A front pad (100) is attached to the front beam (12). A T-shaped front leg (14) is provided on the front end of the beam (12) and a pair of roller sleeves (140) are respectively and rotatably disposed on distal ends of both sides of the leg (14). A front fastener (142) is formed on the inside wall of the leg (14). A hollow connector (16) is welded on the bottom near the rear end of the beam (12). As clearly shown in FIG. 6, two handles (18) are mounted on both ends of the hollow connector (16) by pins (182).

Figure 7:
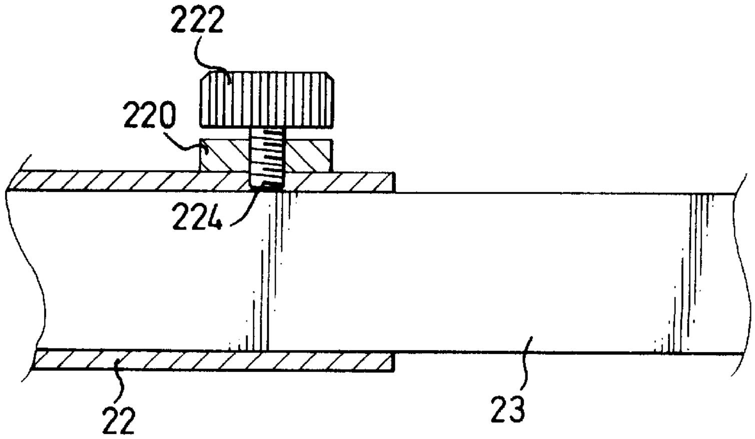
FIG. 7 is a partially sectional view showing an extension beam provided in a rear beam.

The rear frame (20) has a rear beam (22). A rear pad (200) is attached to the rear beam (22). A motor (26) is mounted on the bottom of the rear beam (22) and has a drive shaft (260) extends out of the motor (26). The rear beam (22) is hollow, and an extension beam (23) is slidably received in the rear beam (22). Referring to FIG. 7, the rear beam (22) has a strongback (220) formed on the side thereof. A locking bolt (224) with a knob (222) is screwed into the strongback (220) and rear beam (22) to lock them together. After the knob (222) is loosened, the extension beam (23) can be extended or retracted, and tightening the knob (222) will fix the position of the extension beam (23). A rear telescoping leg (24) is provided on the end of the extension beam (23). The rear telescoping leg (24) has an inner leg (242) adjustably received therein. The height of the inner leg (242) can be adjusted by a pin (244) mounted on the rear telescoping leg (24). A wheel (240) is transversally disposed on the outside of the rear telescoping leg (24).

A sliding bracket (40) is movably mounted on the extension beam (23). The lower portion of the sliding bracket (40) is fixedly connected to the drive shaft (260) of the motor (26), so the sliding bracket (40) can be moved when the motor (26) is operated. A rear fastener (48) is formed on the bottom of the sliding bracket (40). A foot holder (42) is formed on the sliding bracket (40). The foot holder (42) has lower bars (44) integrally formed with the sliding bracket (40). A channel (460) is defined in the foot holder (42). Upper bars (46) are securely provided by means of extending through the channel (460) and rear bars (468) are integrally formed with the upper bars (46). An adjusting handle (462) is provided on the top of the foot holder (46). By the adjusting handle (462), the upper bars (46) and the rear bars (468) can be moved within the channel (460), thus, the foot holder (42) can be adapted to various users according to their foot size.

Figure 3:
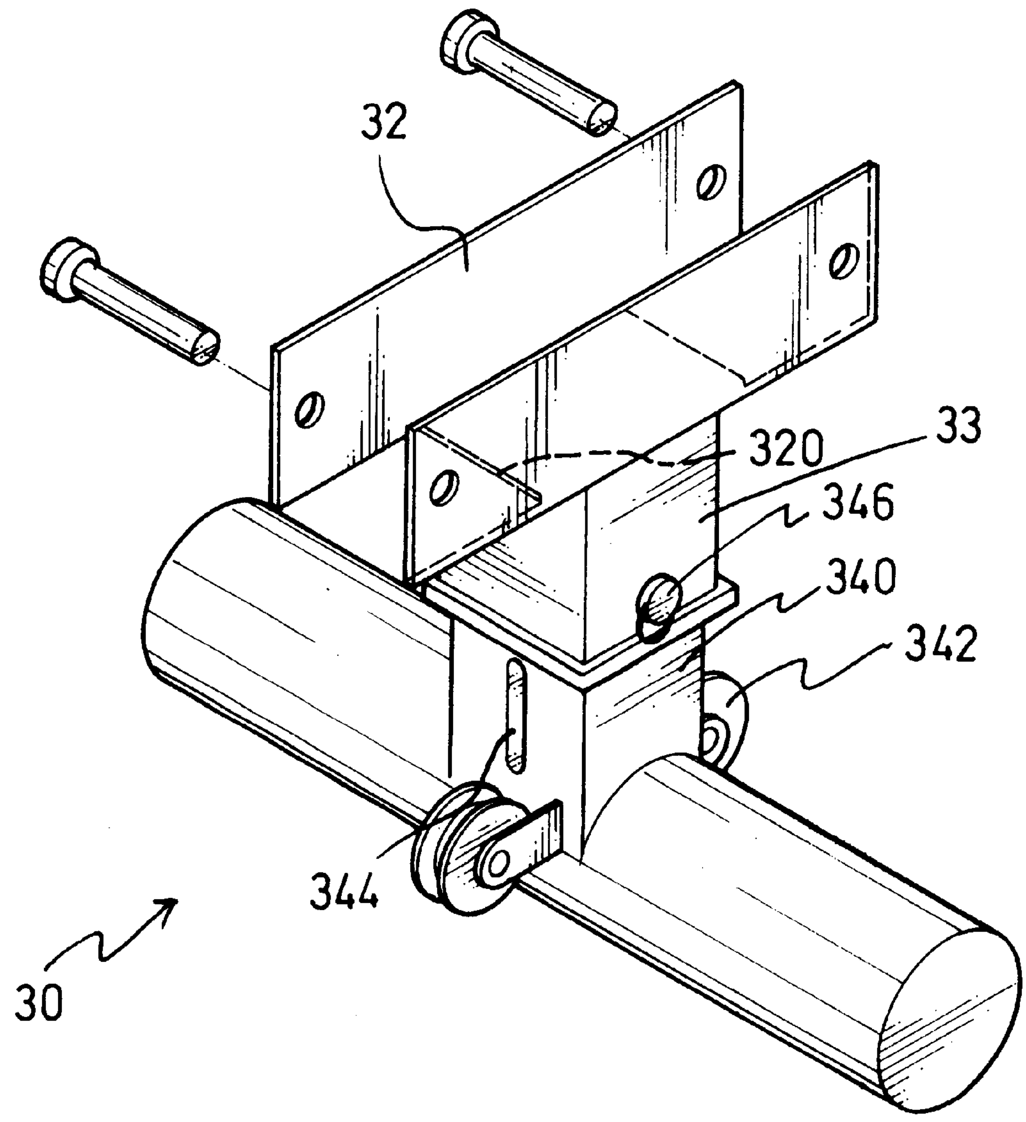
FIG. 3 is a perspective view of a joint of the present invention.

In the present invention, the front frame (10) and the rear frame (20) are connected by a joint (30). FIG. 3 illustrates the joint (30) in detail. The joint (30) has a bracket (32) formed on the upper portion thereof. Both ends of the bracket (32), pivotally engaged with the front and rear beam (12, 22), respectively define notches (320). A middle telescoping leg (33) is formed beneath the bracket (32). There is also an inner leg (340) slidably received in the middle telescoping leg (33). The height of the inner leg (340) can be adjusted by a pin (346) mounted on the middle telescoping leg (33). A slot (344) is defined in the inner leg (340) and two rollers (342) are oppositely mounted below the slot (344).

A rope (50) is provided under the front frame (10) and the rear frame (20). Hooks (52) are attached to both ends of the rope (50). The hooks (52) are attached to the front fastener (142) and the rear fastener (48). The middle portion of the rope (50) passes through the slot (344) of the middle telescoping leg (33) and is reeved over the rollers (342).

Figure 4:
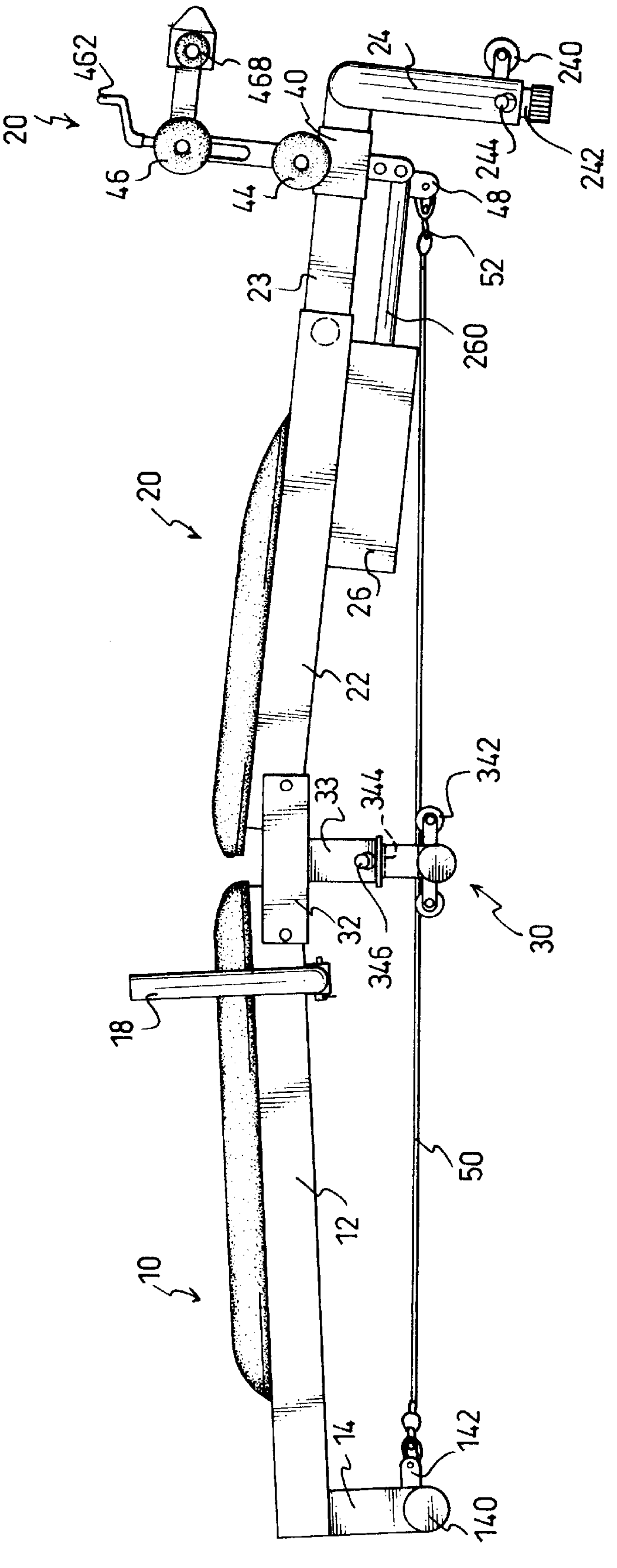
FIG. 4 is a side view showing a motor being started and the joint being raised.
Figure 5:
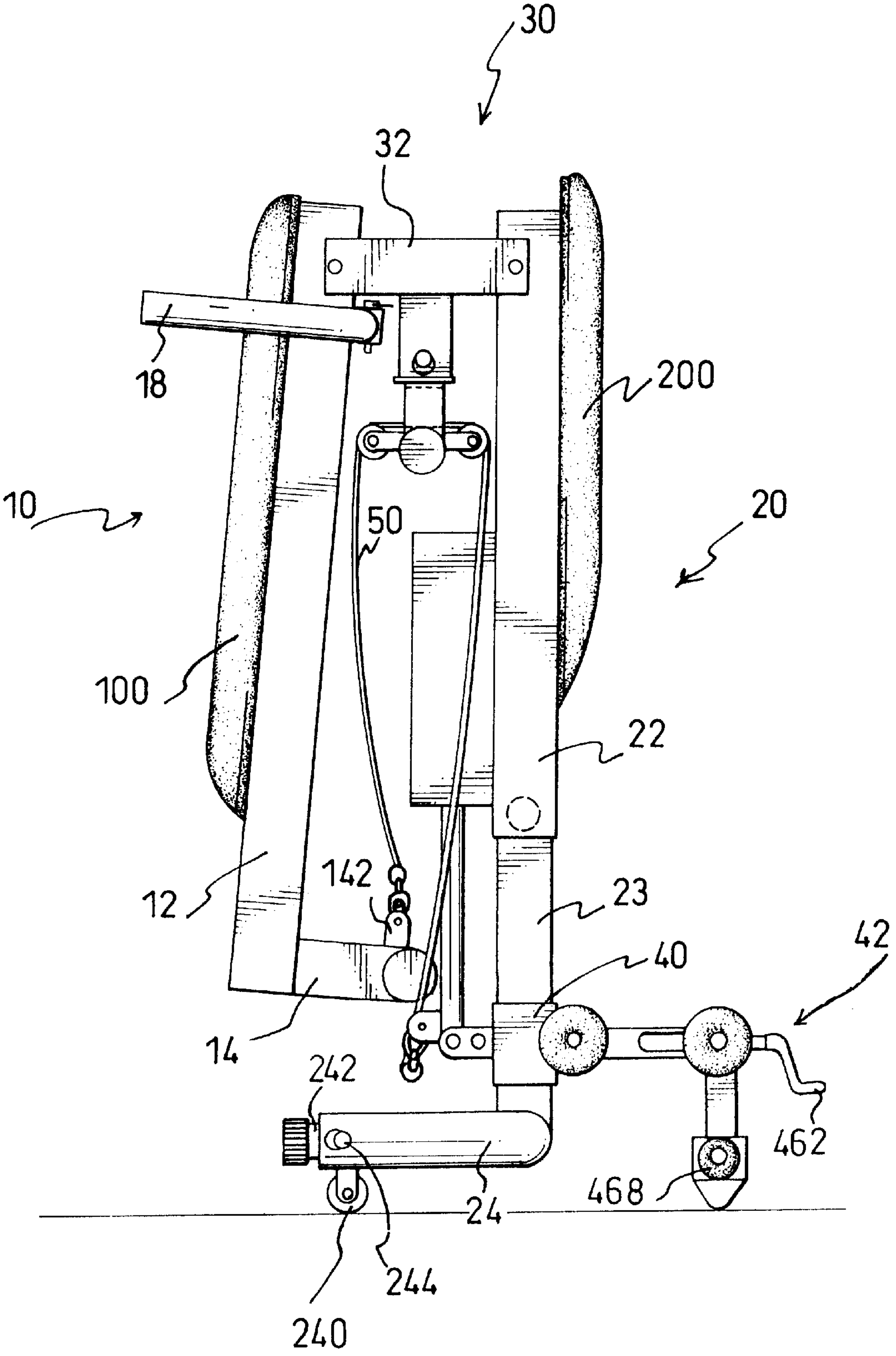
FIG. 5 is a side view showing the present invention being folded.

A user lies on the pads (100, 200) and puts his feet through the upper and lower bars (46, 44) of the foot holder (42). Referring to FIG. 4, when the user starts the motor (26), the drive shaft (260) extends to move the sliding bracket (40) towards the rear telescoping leg (24) along the extension beam (23). Therefore, the body of the user is stretched. With the sliding bracket (40) moving, the rope (50) is gradually tensioned. When the sliding bracket (40) is moved along the extension beam (23) beyond the point where the rope (50) is completely tensioned, the front beam (10) and the rear beam (20) pivot about the joint (30), and the joint (30) is raised upwards. Because the joint (30) is just located at the waist of the user, the lumbar of the user will be raised upwards. This provides therapeutic action that does not exist in the prior art. Of course, if the user does not want to raise his waist, the rope (50) may be released from the fastener (142, 48).

When the front and rear beam (12, 22) are first pivoted, the rope (50) abuts the upper end of the slot (344). Pivoting the beams (12, 20) more, the rope (50) will move downwards to contact the bottom end of the slot (344), thereby stopping the upward movement of the joint (32). At that time, a clutch or detent switch (not shown) in the motor (26) will stop the drive shaft (260) from extending any further. In addition, if the rope (50) looses or breaks, the force causing the joint (30) to rise disappears and the traction machine will drop to the horizontal position. Therefore, the invention is safe in use.

When storing the traction machine, the drive shaft (260) of the motor (26) is retracted to be completely received in the motor (26), the joint (30) is lift up and the front beam (12) and rear beam (22) are thus folded with respect to each other, so the whole machine is folded. The wheel (240) on the outside of the rear beam (22) touches the ground, and it is convenient to move the entire machine for storing.

The advantages of the present invention are:

1. The traction machine can be stored and folded conveniently.

2. The machine can be started by an electric motor, so the user does not need to operate the machine manually.

3. The machine can raise the user's waist.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A foldable electric traction machine comprising:

a front frame having
  a front beam;
  a front pad mounted on the front beam; and
  a front leg formed on an end of the front beam;

a rear frame having
  a rear beam;
  a rear pad mounted on the rear beam;
  an extension beam slidably engaged with the rear beam;
  a rear telescoping support formed on the extension beam; and
  a first inner leg adjustably provided in the rear telescoping support and adjusted by a pin;

a joint, which pivotally connects the front frame and the rear frame, forming a middle telescoping leg;

a second inner leg slidably received in the middle telescoping leg;

a motor mounted beneath the rear beam;

a sliding bracket, which is movably mounted on the extension beam and connected to the motor, having a foot holder formed on the sliding bracket; and a rope having a proximal end and a distal end, said proximal end being connected to said sliding bracket and said distal end being connected to said front leg.

2. The foldable electric traction machine as claimed in claim 1, wherein the front leg is T-shaped has a first end and a second end and said front leg has roller sleeves respectively disposed on both said first end and said second end of said front leg.

3. The foldable electric traction machine as claimed in claim 1, wherein the front frame has a connector mounted beneath the front beam, said connector having a first end and a second end and a first handle being mounted on said first end of the connector and a second handle being mounted on said second end of the connector.

4. The foldable electric traction machine as claimed in claim 1, wherein the rear telescoping leg has a wheel transversally provided on an exterior surface of the rear telescoping leg.

5. The foldable electric traction machine as claimed in claim 1, wherein the rear beam has a strongback formed thereon, said machine further including a locking bolt having a knob, said locking bolt being inserted into the rear beam to fix a position of the extension beam relative to the rear beam.

6. The foldable electric traction machine as claimed in claim 1, wherein the joint further has a bracket where the joint is pivotally connected with the front and rear beams.

7. The foldable electric traction machine as claimed in claim 1, wherein the middle telescoping leg has a pin mounted on the second inner leg to adjust the length of the middle leg.

8. The foldable electric traction machine as claimed in claim 1, wherein the second inner leg defines a slot.

9. The foldable electric traction machine as claimed in claim 8, wherein the second inner leg has two rollers oppositely formed below the slot, the rope being passed through the slot and disposed on the rollers.

10. The foldable electric traction machine as claimed in claim 1, wherein the sliding bracket forms a foot holder thereon, wherein the foot holder defines a channel and a top said foot holder having lower bars integrally formed with the sliding bracket, upper bars provided within the channel and rear bars integrally formed with the upper bars.

11. The foldable electric traction machine as claimed in claim 10, wherein an adjusting handle is provided on the top of the foot holder.

12. The foldable electric traction machine as claimed in claim 10, wherein the front leg forms a front fastener, and the sliding bracket forms a rear fastener, both ends of the rope are fixed to the two fasteners respectively.

* * * * *